United States Patent [19]

DeMarinis

[11] 4,242,346

[45] Dec. 30, 1980

[54] BIS-2N-ALKYLENE TETRAHYDROISOQUINOLINE COMPOUNDS

[75] Inventor: Robert M. DeMarinis, Ardmore, Pa.

[73] Assignee: SmithKline Corporation, Philadelphia, Pa.

[21] Appl. No.: 105,359

[22] Filed: Dec. 19, 1979

[51] Int. Cl.³ .................... A61K 31/47; C07D 401/06
[52] U.S. Cl. .................................. 424/258; 546/140
[58] Field of Search .................... 546/140; 424/258

[56] References Cited

U.S. PATENT DOCUMENTS

| | | | |
|---|---|---|---|
| 2,644,789 | 7/1953 | Shenk, Jr. | 546/140 |
| 2,791,588 | 5/1957 | Collier et al. | 546/140 |

OTHER PUBLICATIONS

Kalaus, et al., "Chemical Abstracts", vol. 72, 1970, col. 100456i.

*Primary Examiner*—Donald G. Daus
*Assistant Examiner*—James H. Turnipseed
*Attorney, Agent, or Firm*—Joseph A. Marlino; William H. Edgerton; Richard D. Foggio

[57] ABSTRACT

Bis-2N-alkylene tetrahydroisoquinoline compounds are inhibitors of phenylethanolamine N-methyl-transferase.

12 Claims, No Drawings

BIS-2N-ALKYLENE TETRAHYDROISOQUINOLINE COMPOUNDS

This invention relates to new bis-2N-alkylene tetrahydroisoquinoline compounds. These components have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

The compounds of this invention are represented by the following formula:

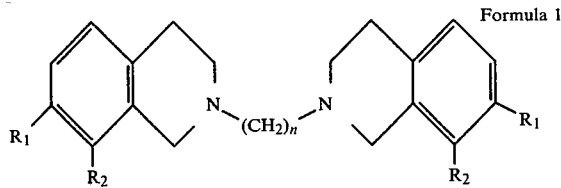

Formula 1 in which:

$R_1$ is chloro or sulfamyl, $R_2$ is chloro and, provided that $R_1$ is sulfamyl, $R_2$ is also hydrogen;

n is a positive integer of from 1 to 8.

Preferred compounds of this invention are represented by Formula 1 above when $R_1$ and $R_2$ are chloro and n=1, 2, and 6.

An advantageous compound of this invention is 2,2'-methylene-bis(7,8-dichloro-1,2,3,4-tetrahydroisoquinoline)dihydrochloride.

The compounds of this invention are prepared by the following procedure:

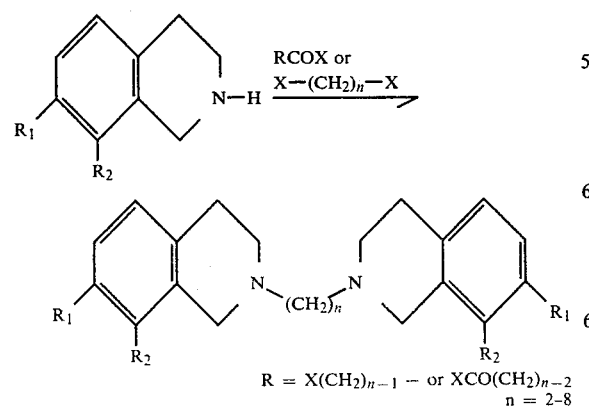

$R = X(CH_2)_{n-1}-$ or $XCO(CH_2)_{n-2}$
n = 2–8
X = Halogen (Cl or Br)

According to the above procedure, when n=2–8 the bis-2-N-alkylene tetrahydroisoquinoline compounds are prepared by a nucleophilic displacement on a dihaloalkane, haloacyl halide or diacyl halide in the presence of an organic or inorganic base, and in an inert solvent such as ethanol, methylene chloride or chloroform. When the nucleophilic displacement occurs on a haloacyl halide, an intermediate amide is formed which is further reacted with the appropriate tetrahydroisoquinoline. The amides obtained from either acyl halide are reduced with a reagent such as, for example, lithium aluminum hydride or diborane. The organic base may be for example, triethylamine and the inorganic base may be magnesium oxide or sodium carbonate. Advantageously the procedure is carried out in the presence of sodium carbonate.

The compounds of this invention when n=1 are prepared by the treatment of the appropriate tetrahydroisoquinoline with formaldehyde.

The nontoxic pharmaceutically acceptable acid addition salts of the compounds of Formula I are similarly useful as the free bases. Such salts are easily prepared by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bis-methylenesalicylate, methanesulfonate, ethanedisulfonate, benezenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The activity of the compounds of Formula 1 is demonstrated by inhibition of phenylethanolamine N-methyltransferase in vitro by the assay procedure described by Pendleton and Snow, *Molecular Pharmacology*, 9:718–725 (1973) at various compound concentrations. For example, at concentrations of $1.0 \times 10^{-4}$ and $1.0 \times 10^{-6}$. A preferred compound of this invention, 2,2'-methylene-bis-(7,8-dichloro-1,2,3,4-tetrahydroisoquinoline)dihydrochloride inhibits phenylethanolamine N-methyltransferase by 99% and 100% respectively.

Following are results of in vitro tests conducted for the PNMT inhibition activity on compounds of this invention.

TABLE 1

In Vitro Inhibition

| Compound | $10^{-4}$ M | $10^{-6}$ M |
|---|---|---|
| n = 1 | 99% | 100% |
| n = 2 | 99% | 47% |
| n = 3 | 100% | 38% |

TABLE 1-continued

In Vitro Inhibition

[Structure: bis-(7,8-dichloro-1,2,3,4-tetrahydroisoquinoline) connected by $(CH_2)_n$ bridge between the two N atoms]

| Compound | $10^{-4}$M | $10^{-6}$M |
|---|---|---|
| n = 5 | 60% | 7% |
| n = 6 | 100% | 82% |
| n = 7 | 90% | 5% |
| n = 8 | 87% | 6% |

The pharmaceutical compositions of this invention to inhibit phenylethanolamine N-methyltransferase comprise a pharmaceutical carrier and, as the active ingredient, a tetrahydroisoquinoline compound of Formula I. The active ingredient will be present in the compositions of this invention in an effective amount to inhibit phenylethanolamine N-methyltransferase.

Preferably, the compositions of this invention contain the active ingredient of Formula I in an amount of from about 50 mg. to about 1000 mg., advantageously from about 100 mg. to about 500 mg., per dosage unit.

The pharmaceutical carrier may be, for example, a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200-400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a bis-tetrahydroisoquinoline compound of Formula I Preferably, the compounds of Formula I are administered in conventional dosage unit forms prepared by combining an appropriate dose of the compound with standard pharmaceutical carriers.

Preferably, the active ingredient of Formula I or II will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of the compounds of this invention and processes for their preparation.

EXAMPLE 1

A solution of 2.37 g. (10 mmol) of 7,8-dichloro-1,2,3,4-tetrahydroisoquinoline hydrochloride salt and 20 ml. of 37% formalin in 100 ml. of water was stirred in an ice bath for thirty minutes. 50 ml. of 5% sodium carbonate solution was added dropwise over 10 minutes and the resulting precipitate was removed by filtration, dissolved in 50 ml. of methylene chloride, dried over magnesium sulfate and filtered. The filtrate was treated with 25 ml. of ethereal hydrogen chloride and allowed to stand in the cold overnight. The resulting precipitate was collected, washed with ether and dried to give 2,2'-methylene-bis-(7,8-dichloro-1,2,3,4-tetrahydroisoquinoline dihydrochloride, melting point 153° C. dec.

EXAMPLE 2

A mixture of 3.75 g. (70 mmol) of magnesium oxide and 8.26 g. (41 mmol) of 7,8-dichloro-1,2,3,4-tetrahydroisoquinoline hydrochloride in 100 ml. of methylene chloride was stirred in an ice bath while 4.75 g. (42 mmol) of chloroacetyl chloride in 25 ml. of methylene chloride was added over 30 minutes. The mixture was allowed to warm to room temperature and stirred overnight. The suspended solids were removed by filtration and the filtrate concentrated to a yellow oil which was dissolved in about 30 ml. of ethanol and placed in the freezer. The resulting crystals were removed by filtration to give solid chloroacetamide.

A mixture of 6.95 g. (25 mmol) of chloroacetamide, 5.9 g. (25 mmol) of 7,8-dichloro-1,2,3,4-tetrahydroisoquinoline and 5.30 g. (50 mmol) of sodium carbonate in 100 ml. of absolute ethanol was refluxed for 4 hours. The mixture was cooled to 0° and filtered. The solid was washed with water and dried to give 10.4 g. of cream colored amide. A suspension of 4.44 g. (10 mmol) of this amide in 300 ml. of dry tetrahydrofuran was stirred under argon with 1.0 g. of lithium aluminum hydride for 1 hour. The mixture was treated with 10 ml. of ethyl acetate followed by 25 ml. of 10% sodium hydroxide. The mixture was evaporated to a residue, treated with 100 ml. of water and extracted with six 50 ml. portions of ethyl acetate. The combined extracts were dried and evaporated to a solid which was triturated with 10 ml. of ethanol. The residue was suspended in 20 ml. of ethanol and treated with 10 ml. of ethereal hydrogen chloride to yield a clear solution which after standing in the cold deposited crystals. The precipitate was removed by filtration, washed with ether and dried to give 2,2'-ethylene-bis-(7,8-dichloro-1,2,3,4-tetrahydroisoquinoline) dihydrochloride having a melting point of 260°-265° C. dec.

EXAMPLE 3

A suspension of 2.38 g. (10 mmol) of 7,8-dichloro-1,2,3,4-tetrahydroisoquinoline and 3.18 g. (30 mmol) of sodium carbonate in 50 ml. of absolute ethanol were refluxed for 5 minutes. To this suspension was added 1.22 g. (5 mmol) of 1,6-dibromohexane and the mixture refluxed overnight. The reaction was cooled and after standing for 36 hours was filtered of solid precipitate. The resulting solid was suspended in 100 ml. of ethyl acetate and treated with 1 g. of magnesium sulfate. The mixture was filtered and the filtrate treated with 10 ml. of ethereal hydrochloric acid. The resulting precipitate was removed by filtration, washed with ether and dried to give 2,2'-hexylene-bis(7,8-dichloro-1,2,3,4-tetrahydroisoquinoline)dihydrochloride having a melting point of 308°–311° C.

EXAMPLE 4

Following the procedure of Example 3, the following compounds:
1,3 dibromopropane
1,7 dibromoheptane myl-8-chloro-1,2,3,4-tetrahydroisoquinoline)dihydrochloride.

EXAMPLE 9

A mixture of 4.12 g. (20 mmol) of 7-sulfamyl-1,2,3,4-tetrahydroisoquinoline and 1.0 g. (25 mmol) of magnesium oxide in 200 ml. of chloroform are stirred at room temperature while 1.82 g. (10 mmol) of adipoyl chloride in 25 ml. of chloroform is added dropwise. After addition is complete the solids are removed by filtration and the filtrate evaporated to give the intermediate amide. This is suspended in dry tetrahydrofuran and treated -continued

| Ingredients | Amounts |
|---|---|
| Lactose | 350 mg. |

The ingredients are mixed and filled into a hard gelatin capsule.

One capsule is administered four times a day.

EXAMPLE 13

| Ingredients | Amounts |
|---|---|
| 2,2'-hexylene-bis(7,8-dichloro-1,2,3,4-tetrahydroisoquinoline)-dihydrochloride | 200 mg. |
| Calcium sulfate dihydrate | 150 mg. |
| Sucrose | 25 mg. |
| Starch | 15 mg. |
| Talc | 5 mg. |
| Stearic Acid | 3 mg. |

The calcium sulfate dihydrate, sucrose and the tetrahydroisoquinoline are thoroughly mixed and granulated with 10% gelatin solution. The wet granules are screened, dried, and then mixed with the starch, talc and stearic acid, screened and compressed into a tablet.

One tablet is administered three times a day.

EXAMPLE 14

| Ingredients | Amounts |
|---|---|
| 2,2'-methylene-bis-(7,8-dichloro-1,2,3,4-tetrahydroisoquinoline)-dihydrochloride | 100 mg. |
| Lactose | 400 mg. |

The ingredients are mixed and filled into a hard gelatin capsule.

One capsule is administered three times a day.

What is claimed is:

1. A chemical compound of the formula:

[Structural formula: a bis-tetrahydroisoquinoline compound with two aromatic ring systems bearing $R_1$ and $R_2$ substituents, connected through $N-(CH_2)_n-N$ linker]

in which:
$R_1$ is chloro or sulfamyl; $R_2$ is chloro and, provided that $R_1$ is sulfamyl, $R_2$ is also hydrogen, and n is a positive integer from 1 to 8, or a pharmaceutically acceptable acid addition salt thereof.

2. A chemical compound of claim 1 in which $R_1$ is chloro.

3. A chemical compound of claim 2 in which $n=6$.

4. A chemical compound of claim 1 in which $R_1$ is sulfamyl.

5. A chemical compound of claim 4 in which $R_2$ is hydrogen and $n=1$.

6. A chemical compound of claim 4 in which $R_2$ is chloro and $n=1$.

7. A chemical compound of claim 2 in which the compound is 2,2'-methylene-bis(7,8-dichloro-1,2,3,4-tetrahydroisoquinoline)dihydrochloride.

8. A pharmaceutical composition in dosage unit form for inhibiting phenylethanolamine N-methyltransferase comprising a pharmaceutical carrier and a chemical compound as defined in claim 1.

9. A pharmaceutical composition in dosage unit form for inhibiting phenylethanolamine N-methyltransferase comprising a pharmaceutical carrier and a chemical compound as defined in claim 2.

10. A method of inhibiting phenylethanolamine N-methyltransferase which comprises administering to an animal requiring said inhibition an amount sufficient to produce said inhibition of a chemical compound as defined in claim 1.

11. A method of inhibiting phenylethanolamine N-methyltransferase which comprises administering to an animal requiring said inhibition an amount sufficient to produce said inhibition of a chemical compound as defined in claim 2.

12. A method of inhibiting phenylethanolamine N-methyltransferase which comprises administering to an animal requring said inhibition a dosage unit containing from about 50 mg. to about 1000 mg. of a chemical compound as defined in claim 1.

* * * * *